United States Patent [19]

Merril

[11] Patent Number: 4,703,016

[45] Date of Patent: Oct. 27, 1987

[54] SILVER STAIN FOR RAPID, QUANTITATIVE DETECTION OF POLYPEPTIDES AND NUCLEIC ACIDS

[75] Inventor: Carl R. Merril, Rockville, Md.

[73] Assignee: The United States of America as represented by the Department of Health and Human Services, Washington, D.C.

[21] Appl. No.: 859,822

[22] Filed: May 5, 1986

[51] Int. Cl.$^4$ .................... G01N 21/77; G01N 33/52; G01N 33/58
[52] U.S. Cl. ......................................... 436/86; 422/61; 436/94; 436/169; 436/174; 436/905
[58] Field of Search ...................... 436/86, 87, 88, 94, 436/164, 169, 174, 175, 177, 178, 515, 905; 422/61

[56] References Cited

U.S. PATENT DOCUMENTS

| | | | |
|---|---|---|---|
| 4,405,720 | 9/1983 | Merril | 436/86 |
| 4,416,998 | 11/1983 | Adams et al. | 436/86 |
| 4,434,234 | 2/1984 | Adams et al. | 436/86 |
| 4,554,254 | 11/1985 | Krystal | 436/86 |
| 4,555,490 | 11/1985 | Merril | 436/86 |
| 4,575,452 | 3/1986 | Lee et al. | 436/86 X |

OTHER PUBLICATIONS

Merril et al., Anal. Biochem., vol. 110, No. 1, pp. 201–207, 1981.
Yuen, et al., (1982), Anal. Biochem., 126:398–402, "A Silver-Staining Technique for Detecting Minute Quantities of Proteins on Nitrocellulose Paper: Retention of Antigenicity of Stained Proteins".
Moeremans, et al., (1985), Anal. Biochem, 145:315–321, "Sensitive Colloidal Metal (Gold or Silver) Staining of Protein Blots on Nitrocellulose Membranes".
Merril et al., 1982, Electrophoresis, 3:17–23.
Merril et al., 1984, Electrophoresis, 5:289–297.

Primary Examiner—Barry S. Richman
Assistant Examiner—Robert J. Hill, Jr.
Attorney, Agent, or Firm—Holman & Stern

[57] ABSTRACT

A simple, positive image forming silver stain which takes less than 15 minutes to perform is disclosed for the detection of nanogram quantities of proteins and DNA on membranes and thin layer plates. This stain demonstrates a reproducible curvilinear relationship between silver density and the amount of protein or DNA, over an averaged concentration range from 1 nanogram to 300 nanograms for proteins and 10 nanograms to 700 nanograms for DNA. The ease of staining proteins and DNA on membranes, combined with the stain's sensitivity and reproducibility, permits quantitative determination and assay of proteins and DNA.

5 Claims, 3 Drawing Figures

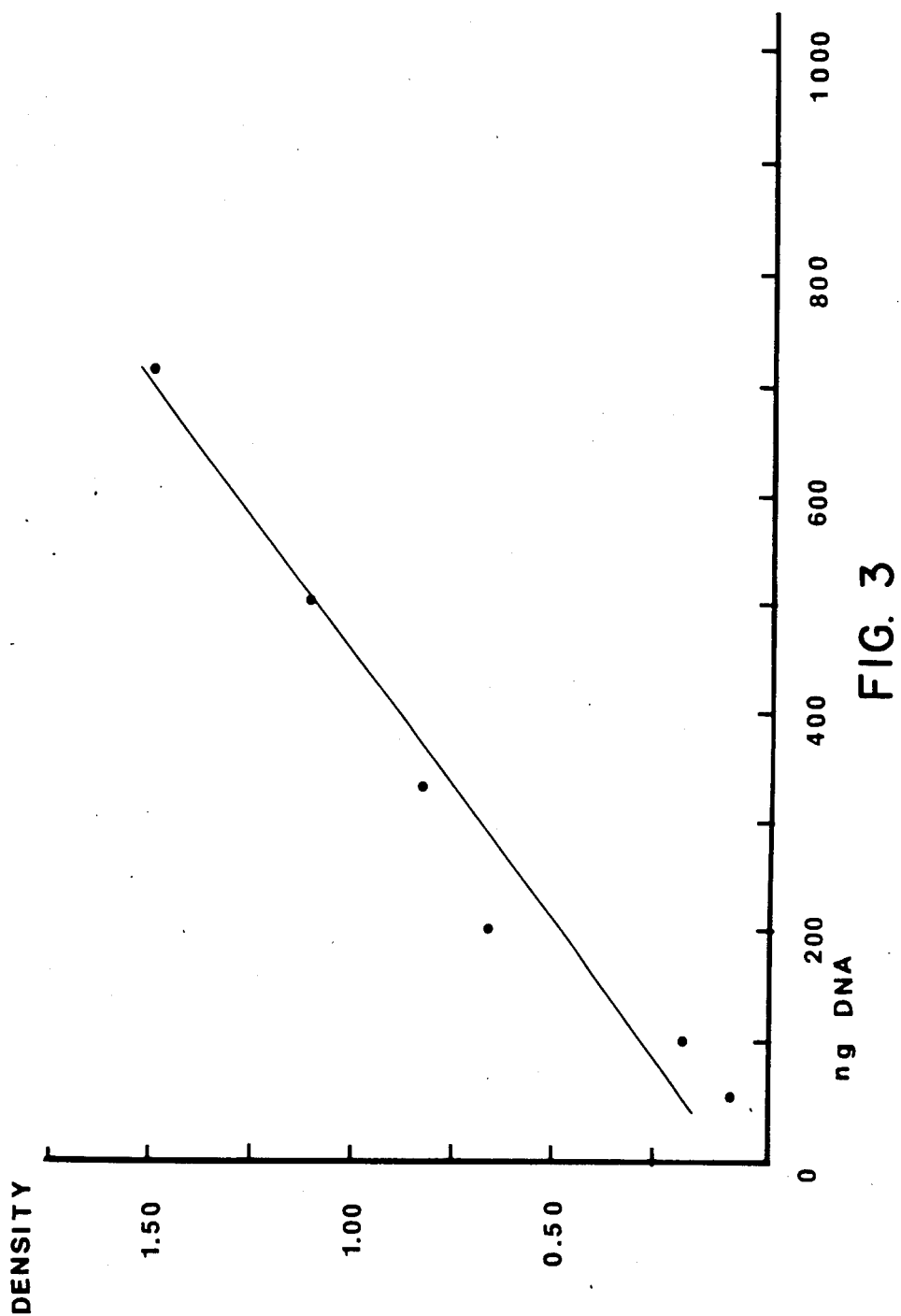

SILVER STAIN FOR RAPID, QUANTITATIVE DETECTION OF POLYPEPTIDES AND NUCLEIC ACIDS

BACKGROUND OF THE INVENTION

1. Technical Field

The present invention is related generally to the detection of polypeptides and nucleic acids separated by chromatographic or electrophoretic procedures. More particularly, the present invention is related to a unique silver stain and a simple, rapid and quantitative method for detecting nucleic acids and proteins on commonly available membranes or thin layer plates and the like employed as supporting and separation medium using the silver stain of the present invention.

2. State of the Art

Silver stains for the detection of proteins such as described in U.S. Pat. Nos. 4,405,720 and 4,555,490 are more sensitive than the organic stains such as Coomassie blue or amido black. However, the prior art Holman & Stern, Chartered Folio P49616 silver stains for the detection of proteins on membranes either result in relatively dense background staining (Merril et al., *Electrophoresis* 5:289–297, 1984), or require considerable time to develop. For instance, the method of Yuen et al., *Anal Biochem* 126:398–402 (1982) requires 45 minutes of manipulations in addition to an overnight reaction. Background staining problems have also limited the use of stains which employ colloidal gold and silver, restricting their use to nitrocellulose membranes. Furthermore, the colloidal gold and silver stains require 4 and 2 hour incubations, respectively (Moeremans et al., *Anal Biochem.* 145:315–321, 1985). Additionally, the prior art silver stains produce a combination of negative and positive images which make quantitation of the polypeptide difficult.

SUMMARY OF THE INVENTION

It is, therefore, an object of the present invention to provide a positive image producing silver stain for rapid and quantitative detection of polypeptides and nucleic acids.

It is a further object of the present invention to quantitatively determine the proteins or nucleic acids separated by electrophoresis on membranes or thin layer plates.

It is yet another object of the present invention to be able to stain and detect nucleic acids and proteins in a time period of less than fifteen minutes.

Other objects and advantages will become evident as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF INVENTION

Figure 1:
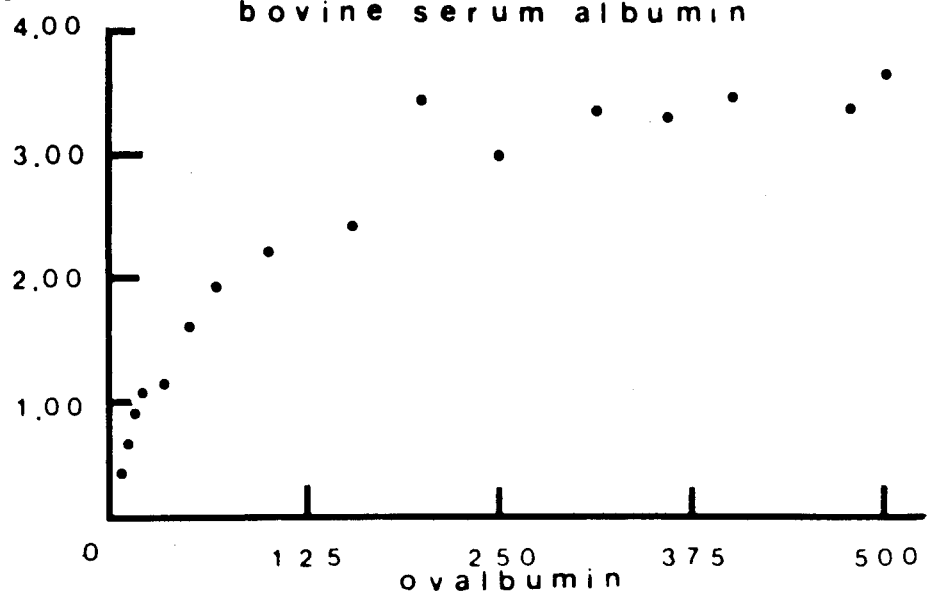
FIG. 1 represents total silver densities plotted against the amount of protein for six purified proteins, in native and denatured states. The purified proteins were diluted and spotted on nitrocellulose membranes with 22 micron pore size in this study. Staining and densitometric analysis are described in the text. Denaturation was effected by using heat in the presence of SDS.
Figure 1:
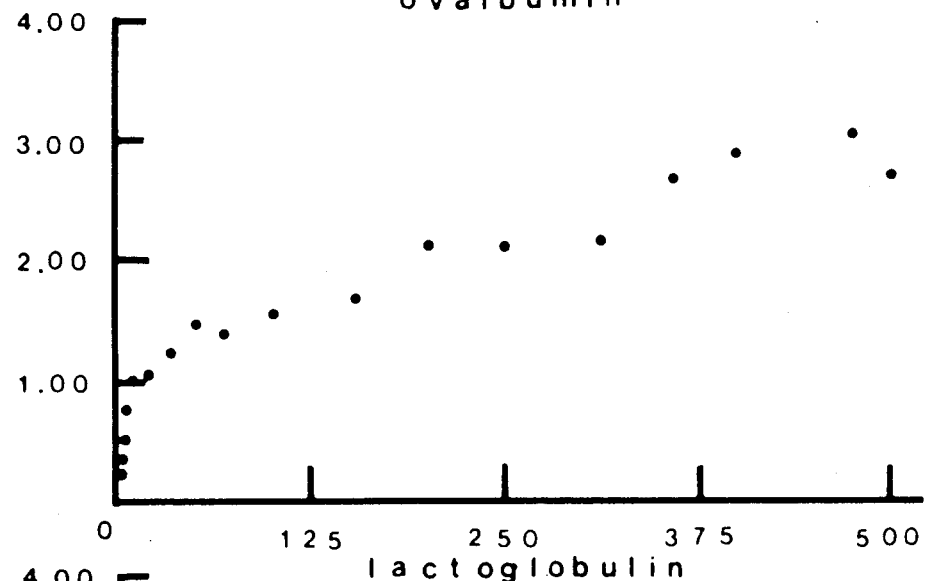
Figure 1:
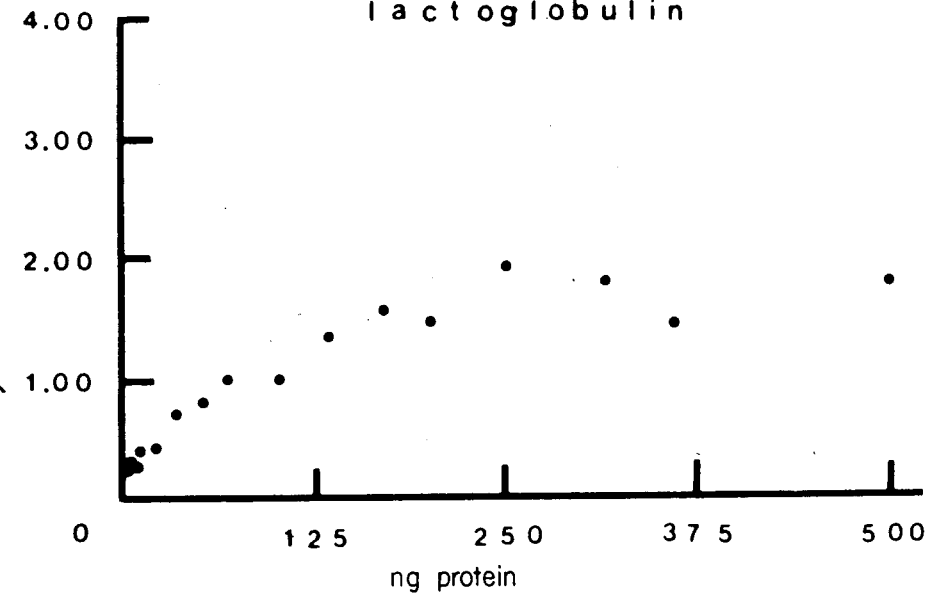

The above and other objects and advantages of the present invention are achieved by a silver stain comprising a staining system consisting essentially of separate aqueous solutions in distilled or deionized water of:

(a) cupric acetate up to saturating concentration;

(b) about 10–50% v/v acetic acid comprising about 0.01 to 0.1M NaCl and about 0.01 to 0.2M citric acid;

(c) about 10–50% v/v acetic acid comprising about 0.01–0.5M $AgNO_3$;

(d) about 0.01–0.3M hydroquinone comprising about −0.01% to 10% v/v of a 37% concentrated formaldehyde stock solution; and (e) about 0.01 to 0.5M $Na_2S_2O_3$ solution;

said system producing a positive image of electrophoretically separated proteins and nucleic acids fixed on thin electrophoretic separation medium and a method for rapid, quantitative staining of proteins separated by electrophoresis on a suitable medium such as membranes, thin layer plates and the like.

Unless specifically defined otherwise, all scientific and technical terms used herein have the same meaning as generally understood by one of ordinary skill in the art to which the invention belongs. All publications mentioned hereunder are incorporated herein by reference.

Although any similar or equivalent methods and materials may be used or adopted in the practice of the invention or for the tests described herein, the preferred materials and methods are now described.

The term "separation or support medium" as used herein means any medium which allows separation of proteins or nucleic acids when said medium is subjected to electrophoretic, chromatographic, adsorption, blotting procedures and the like. Such media are well known in the art, usually commercially available and include materials such as thin and ultrathin membranes, particularly cellulose, nitrocellulose, cellulose acetate, nylon membranes, standard thin layer plates, thin slabs of gels, glass fibre and the like. The thickness of the support medium could range from about 25 $\mu$m to about 2 mm, the preferred range being from about 80 to 500 $\mu$m.

By combining silver photo-development and chemical-development methods, a stain has been developed which can detect proteins and nucleic acids in the nanogram range, be performed in a time requiring less than fifteen minutes, and results in minimal background staining. This stain utilizes: a silver halide to provide a light sensitive detection medium and prevent the loss of silver ions from membranes or thin layer plates; photoreduction to initiate the formation of silver nucleation centers; and chemical-development to provide a high degree of sensitivity by depositing additional silver on the silver nucleation centers (formed by the photo-reduction of the silver halide). This stain displays an average detection sensitivity of about 1 ng of protein or about 10 ng of DNA.

The reproducible curvilinear response and sensitivity in the nanogram range of this silver stain, permits its use in the qualitative detection of proteins and DNA on membranes and its application as a method for rapid quantitative determination of small amounts of protein or DNA.

MATERIALS AND METHODS

The purified proteins alpha-chymotrypsin, beta-lactoglobulin, ovalbumin, hemoglobin, and carbonic anhydrase were obtained from Sigma Chemical Co., St. Louis, Mo. as were the RNA, nucelotides, nucleosides and purine and pyrimidine bases. Bovine serum albumin was from Nutritional Biochemical and the standard DNA was from Calbiochemical. The chemicals used in silver staining were Baker Chemical sodium chloride, and acetic acid; Mallinckrodt silver nitrate; MCB cupric acetate; Fisher, sodium thiosulfate; Sigma, citric acid; and Eastman Kodak, hydroquinone. The Coomassie blue is easily available commercially. The Avicel thin layer plates were from Analtech, while the nitrocellulose, and cellulose acetate, membranes were from Schleicher and Schuell. Nylon membranes were from DuPont NEN. Dilutions of amino acids, peptides, nucleic acids, and homopolymers were made from gravimetrically prepared stock solutions (2 mg/ml). These stock solutions were weighed on an analytical balance to an accuracy of 0.005 mg and dissolved in appropriate solutions measured to an accuracy of 0.005 ml. In experiments which utilized denatured proteins the native proteins were mixed with 0.5% sodium dodecylsulfate (SDS), and heated for about 4 mins at about 95° C. They were then cooled to room temperature (22°-25° C.), spotted and then fixed on the membranes as described infra. To eliminate potential staining artifacts which might be caused by the growth of adventitious organisms, all sample solutions were made by utilizing sterile technique and were used on the day that they were prepared.

Fixation procedures. Proteins were fixed prior to staining by drying at room temperature, followed by heating at about 110° C., for about 10 minutes. It was found that this method of fixation was the most efficient, particularly for the small peptides. Direct application of the proteins to nitrocellulose membranes, the method preferred for quantitative protein assay, required spotting small aliquots of 5 μl or less (to prevent excessive spreading of the sample) onto the membranes. The membranes were then suspended across an open dish or tray during the protein spotting procedure and they remained in this position until dry (to prevent aborption through the membrane to another surface).

Coomassie staining was performed as follows. The membranes containing "fixed" proteins were placed in a solution containing: 0.1% w/v of Coomassie blue stain for about 5 minutes, followed by destaining with several changes of water until clear. The membranes were then soaked for about 2 minutes in a solution containing 10% v/v methanol, 5% v/v acetic acid and 0.05% w/v Coomassie blue. Final destaining was accomplished by soaking the membranes in a solution containing 10% v/v methanol, and 5% v/v acetic acid for about 10-15 minutes.

STAINING: Silver Staining was performed as follows: The procedure is applicable to both the membrane as well as to the thin layer plates.

Step 1. The membrane containing the fixed protein samples were placed in a cupric acetate solution (0.4M) for one minute.

Step 2. The membrane from step 1 was then transferred to a 10% v/v acetic acid solution containing 0.03M NaCl and 0.1M citric acid for an additional minute.

Step 3. The membrane was then transferred to a 10% v/v acetic acid solution containing 0.1M $AgNO_3$ and irradiated for one minute by a uniform light source. An Aristo T-12 lamp containing a W45 daylight fluorescent lamp, approximately equivalent to 1500 watts tungsten was used in these experiments (Aristo Grid Lamp Products, Inc. New York, 11050).

Step 4. The membrane was removed from the silver nitrate solution (10% v/v acetic acid solution containing 0.1M $AgNO_3$) and again placed in the 10% v/v acetic acid solution containing 0.03M NaCl and 0.1M citric acid for one minute.

Step 5. The membrane was then transferred back to the silver nitrate solution of step 4 and irradiated for three minutes by the uniform light source mentioned above.

Step 6. A protein image was developed by transferring the irradiated membrane into a 0.2M hydroquinone solution containing 4% v/v of a concentrated formaldehyde stock solution (37%), for one minute, or until the membrane developed an even dark browncolor.

Step 7. Image development was followed by a one minute water rinse and then a five minute immersion in a basic solution containing 0.06M $Na_2S_2O_3$. The membrane was gently agitated every 30 seconds during this immersion.

Step 8. The membrane was then washed briefly by a stream of tap water which was directed to flow parallel to the surface of the membrane, to wash off the unbound silver. If the water flow was directed perpendicular to the membrane surface, then the unbound metallic silver became embedded in the membrane support, resulting in an uneven background stain. It is noted that the water used in Steps 1-7 was distilled or deionized $H_2O$.

Densitometry. Membranes or thin layer plates were photographed next to a calibrated optical density standard (from the National Bureau of Standards) on 120 mm Kodak Tri-X film. A Mamiya RB67 Pro camera was used with a 140 mm macro lens. The membranes were transilluminated with an Aristo T-12 lamp containing a W45 daylight fluorescent lamp. The photographic images were scanned and digitized at a resolution of 100 μm with an optronics 1000HS scanning densitometer at the 0-2 optical density setting. The digitalized images were analysed with an image processor, DeAnsa Systems, Inc., model IP 5000, and a PDP 11/60 Digital Equipment Co. computer. Image densities were normalized for variations in photography and densitometric digitization by use of the calibrated density standard that was incorporated in each photograph. Density in this analysis is defined as follows: one unit of density is the density that permits the transmission of 1% of the incident light. The density scale is logarithmic so that, for example, a density of 2 permits the transmission of only 0.1% of the light. About 6.5 ng of silver per mm in a photographic emulsion corresponds to a density of one unit (Goodno et al., *Anal. Biochem.* 115:203-211, 1981). Proteins or DNA visualized by staining were quantitatively analysed by outlining each digitized protein or DNA image with a polygon, so adjusted that it closely surrounded each image. The total density was measured by multiplying the average density of all the picture elements bounded by the polygon, and the total area of the polygon.

As can be seen from the results presented in Table 1, in the presence of proteins or nucleic acids, the stain of the present invention which produced a brownish to black image on membranes, detected, on the average, 1 ng of protein or 10 ng of DNA. Of the proteins tested, the stain showed the greatest sensitivity for ovalbumin, detecting as little as 0.05 ng on nitrocellulose membranes, whereas for hemoglobin the stain required 5 ng for detection. Sensitivity for nucleic acids was not as great as that for proteins with detection limited to about 10 ng of DNA. This stain demonstrated the capacity to detect proteins and nucleic acids that were applied to membranes either by spotting, electrophoretic transfer, or by blotting. It was also capable of detecting peptides separated by electrophoresis and chromatography on cellulose thin layer plates. The lowest backgrounds were achieved with 0.20 micron cellulose nitrate membranes. Slightly higher backgrounds were observed with 0.45 micron cellulose nitrate and cellulose acetate membranes, while nylon membranes gave the highest backgrounds.

TABLE 1

Staining Characteristics of Six Native Purified Proteins and DNA.

| Protein | Min. det. (ng) | Linear Range (ng) | Correlation Coef. | DP* | Slope |
|---|---|---|---|---|---|
| Bovine Serum Alb. | 1.00 | 20–200 (10×) | .972 | 7 | .0119 |
| Ovalbumin | 0.05 | 5–500 (100×) | .984 | 15 | .0044 |
| B-Lactoglobulin | 1.00 | 7–250 (25×) | .978 | 12 | .0062 |
| a-Chymotrypsin | 0.10 | 10–357 (36×) | .989 | 13 | .0037 |
| Carbonic Anhydrase | 0.50 | 20–250 (13×) | .969 | 8 | .0029 |
| Hemoglobin | 5.00 | 20–250 (12.5×) | .977 | 8 | .0027 |
| DNA | 10.00 | 50–710 (14.2×) | .979 | 6 | .0021 |

Figures 1, 2:
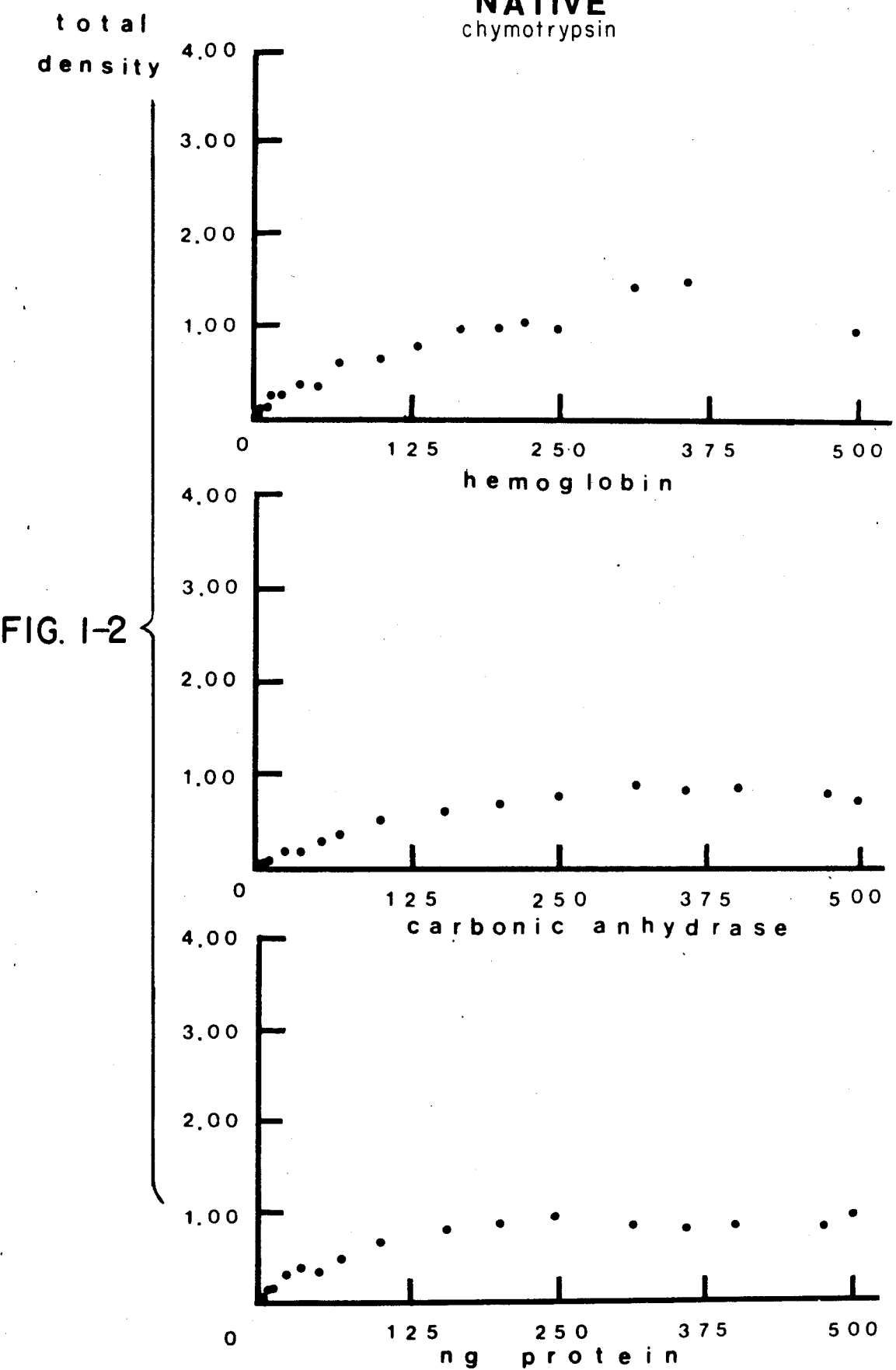
FIG. 2 represents the reciprocals of the total silver densities plotted against the reciprocals of the concentrations of native proteins. These plots represent the same data as that plotted in FIG. 1 for the native proteins.
Figures 1, 2, 3:
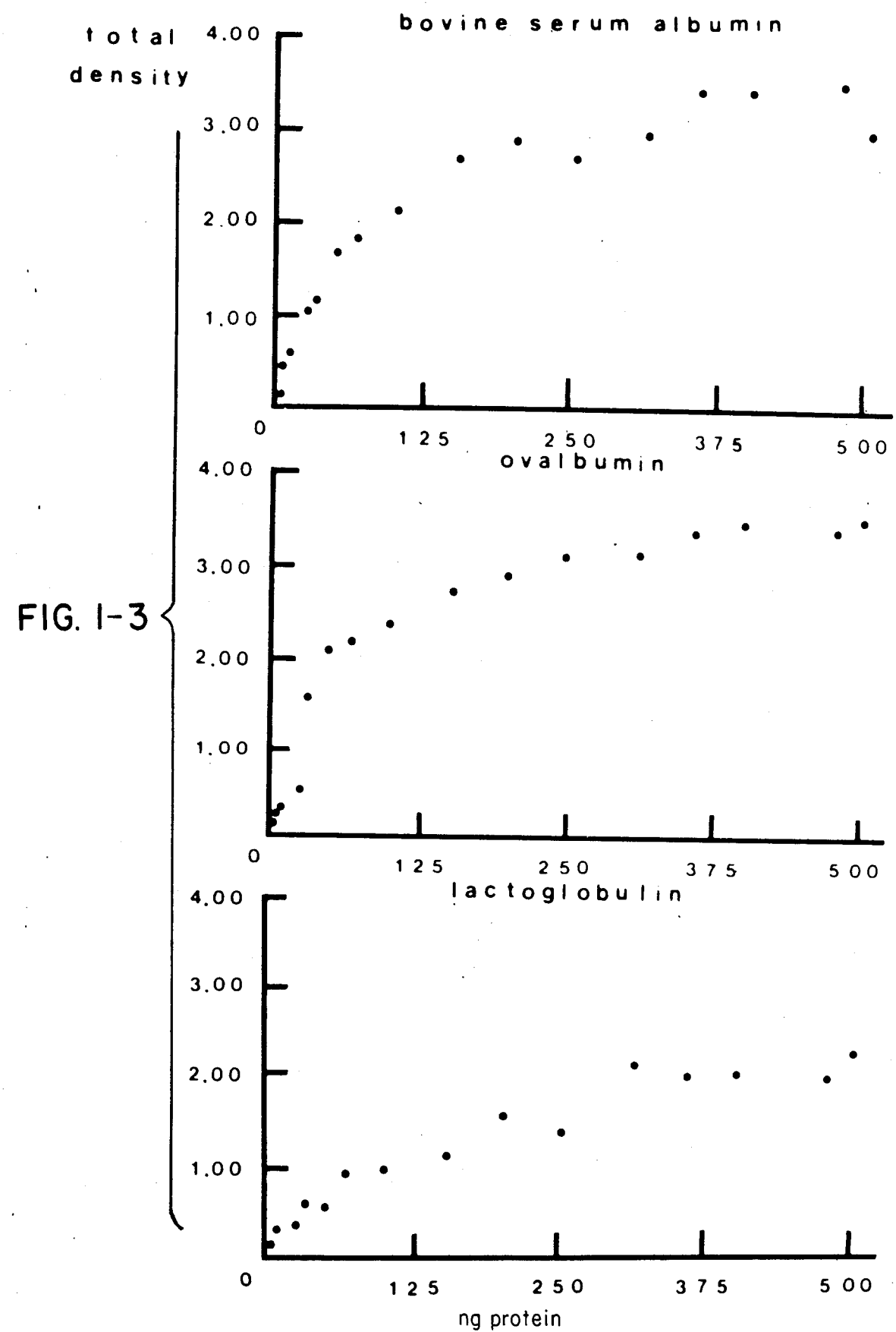
FIG. 3 represents total silver densities plotted against the amount of DNA. The purified DNA was diluted and spotted on a membrane with 22 micron pore size. Staining and densitometric analyses were as described in the text.
Figures 1, 2, 3, 4:
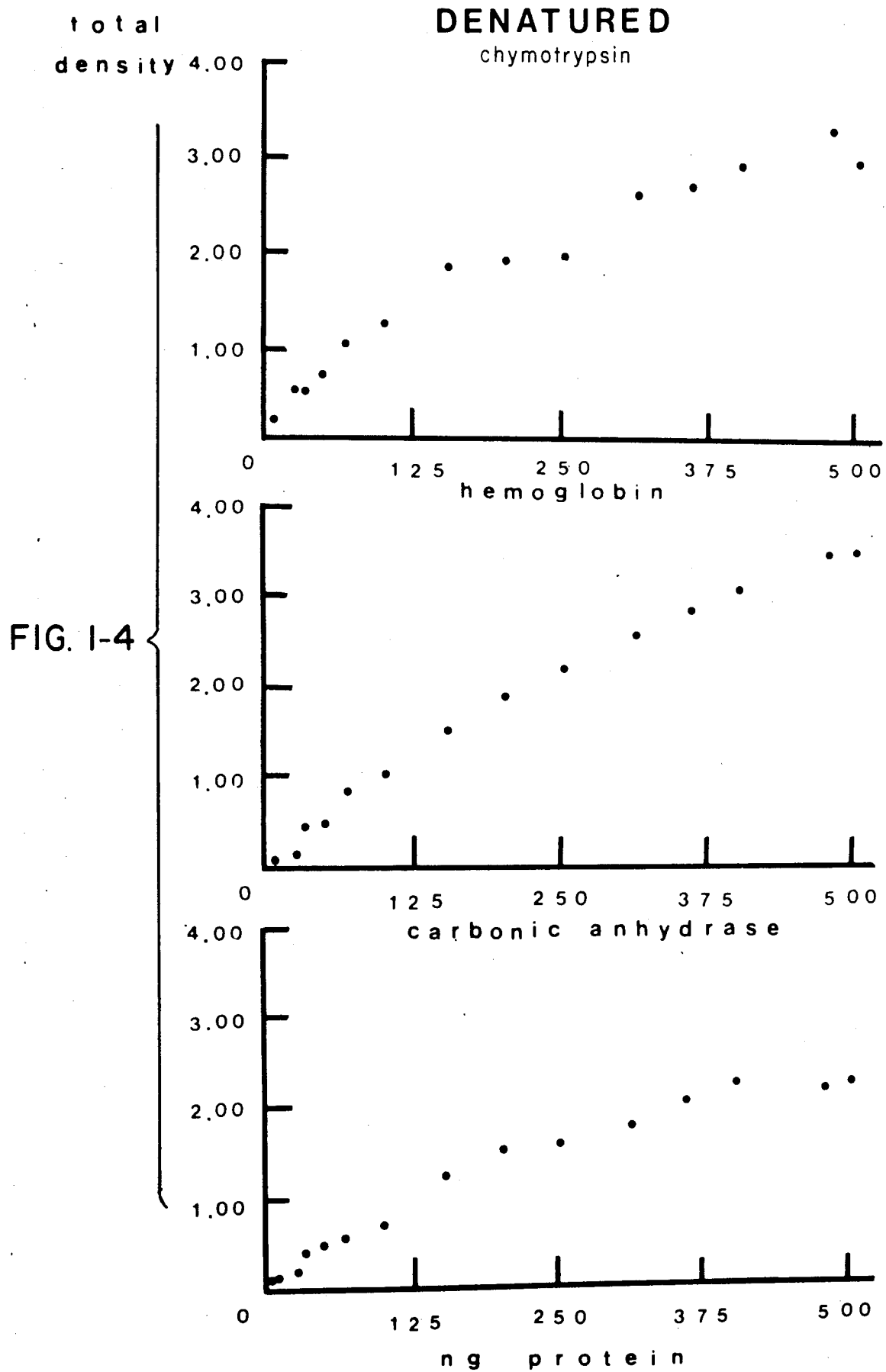
Figures 1, 2:
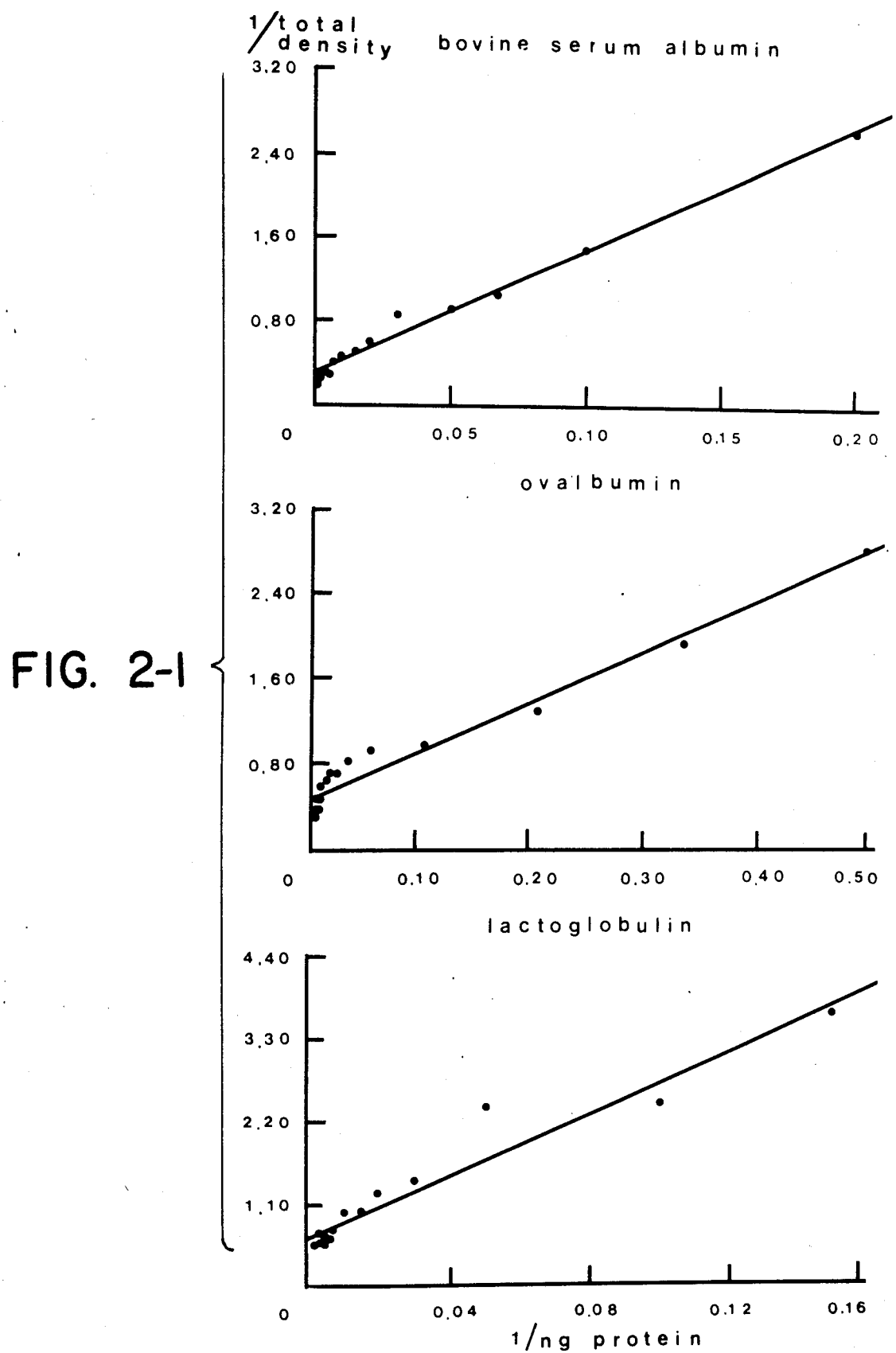
Figure 2:
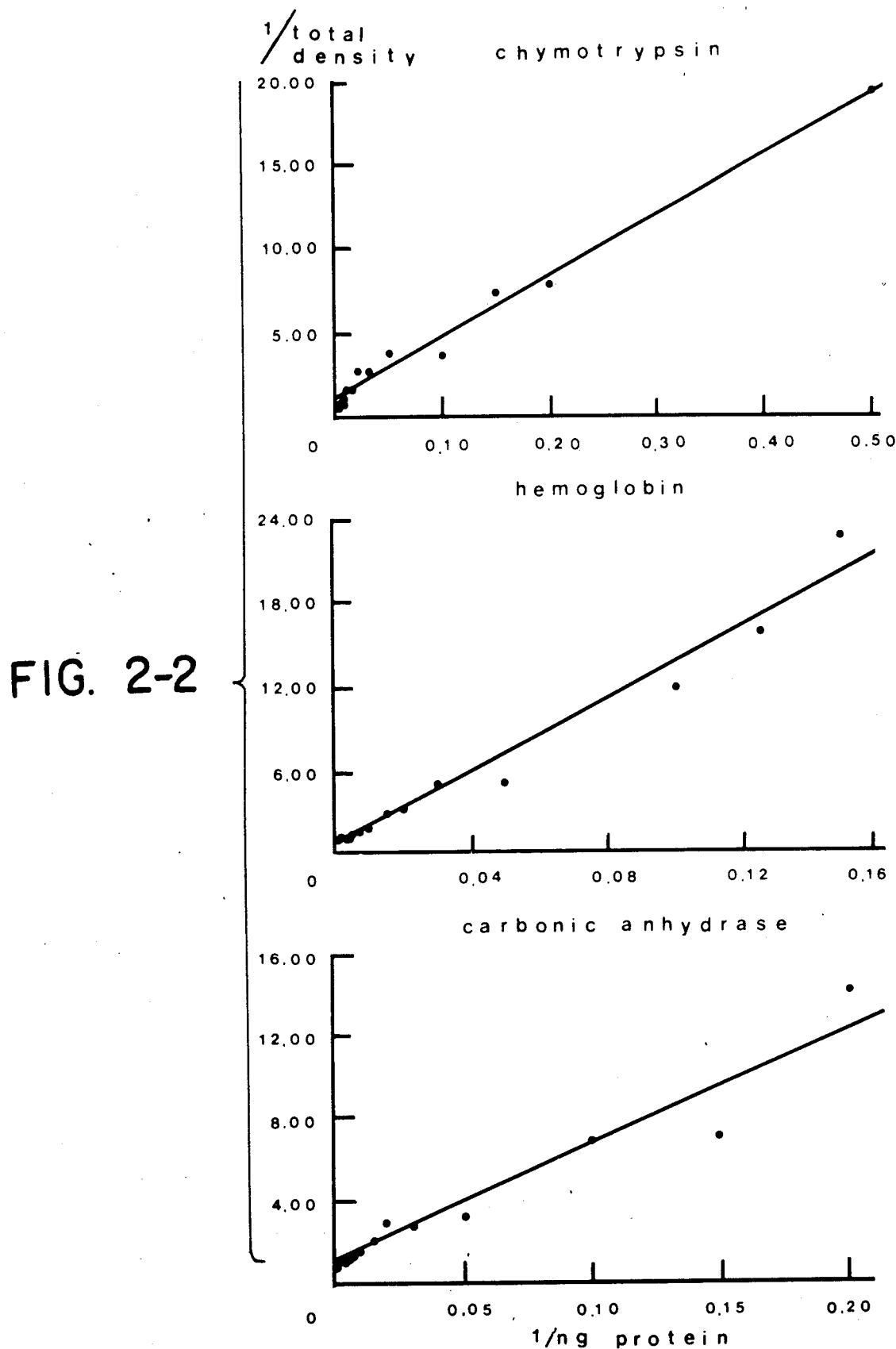

*DP represents the number of data points measured in the linear portions of the curves for the native proteins represented in figure 4. These curves present the relationship between the developed silver stain density and the concentration of protein or DNA. The P value was <.001 for the correlation coefficients of the data points. Each data point in this table represents the average value obtained from a minimum of 4 experimental determinations.

Purified proteins displayed characteristic staining curves, when silver stain densities were plotted against varying amounts of each protein (FIG. 1), as had been observed in previous silver stains studied (Switzer et al., *Anal Biochem.* 98:231–237, 1979; Merril et al., *Electrophoresis* 3:17–23, 1982; Poehling et al., *Electrophoresis* 2:141–147, 1981). Each of these staining curves was characterized by a rapid increase in the density of the silver stain between an average of 3 ngs to an average of 14 ngs and then the staining curves became fairly linear over an average concentration range of 32 fold. For the native proteins, the average linear range was between 14 ngs and 343 ngs. Bovine serum albumin had a staining slope, in the linear portion of the curve, that was 2.7 times as steep as that of ovalbumin (Table 1). In previous studies utilizing chemical development, and no photodevelopment, these relations were reversed (Merril et al., supra; Poehling et al., supra). However, these previous studies involved proteins that were separated and denatured by electrophoresis and sodium dodecyl sulfate (SDS) on polyacrylamide gels. When the proteins in the present study were stained, after being denatured by exposure to SDS and heat, the difference in the staining slope, between bovine serum albumin and ovalbumin, was reduced to a factor of 1.5. Denaturation also resulted in a general increase in silver stain intensity, and an average 1.3 fold increase of sensitivity. Some proteins such as bovine serum albumin and β-lactoglobulin displayed large increases in sensitivity (20 and 10 fold respectively) (Table 2 and FIG. 1).

TABLE 2

Staining Characteristics of Denatured Purified Proteins.

| Protein | Min. det. (ng) | Linear Range (ng) | Correlation Coef. | DP* | Slope |
|---|---|---|---|---|---|
| Bovine Serum Alb. | 0.05 | 50–475 (9.5×) | .947 | 10 | .0046 |
| Ovalbumin | 0.05 | 50–500 (10×) | .958 | 11 | .0033 |
| B-Lactoglobulin | 0.10 | 1–500 (500×) | .954 | 16 | .0043 |
| a-Chymotrypsin | 0.50 | 10–500 (50×) | .972 | 14 | .0047 |
| Carbonic Anhydrase | 0.25 | 1–500 (500×) | .974 | 16 | .0048 |
| Hemoglobin | 5.00 | 10–500 (50×) | .990 | 14 | .0074 |

*DP represents the number of data points measured in the linear portions of the curves of the denatured proteins represented in figure 4. These curves present the relationship between the developed silver stain density and the concentration of denatured protein. The P value was <.001 for the correlation coefficients of the data points. Each data point in this table represents the average value obtained from a minimum of 4 experimental determinations.

The capacity and sensitivity of detecting as little as 10 ngs of DNA is demonstrated in FIG. 3 and Table 1. A linear relationship was observed between the stain density and the amount of DNA over about 14 fold range of DNA concentration.

In quantitative studies using purified proteins, it was found that most proteins can be detected with a reproducible curvilinear relationship from 5 ng to 790 ngs (Table 3). Quantitative microdensitometry, with native proteins, demonstrated an average linear 33 fold protein concentration range that varied between 100 fold for ovalbumin to 10 fold for Bovine serum albumin (Table 1). Denatured proteins had an average 186 fold linear range (Table 2). Although the linear region for most proteins begin between 5 to 20 nanograms, the stain is capable of detecting on the average 1.27 ng of native protein or 0.99 ng of denatured protein, and for certain proteins such as ovalbumin, as little as 0.05 ng of protein can be detected in both the native and denatured states. By employing the use of curve-fitting techniques, as described by Coakley and James, *Anal. Biochem.* 115:203–211 (1978) for analysis of the similar nonlinear relationship found in the Folin-Lowry method of protein estimation *J. Biol. Chem.* 193:265–275 (1951), the concentration of a protein can be determined graphically from the relationship, $$D^{-1} = a + b[P]^{-1} \quad [1]$$

in which [P] is the concentration of a protein, D is the total silver stain density of the stained protein and a and b are the constants. With careful measurement of total stain densities, estimates of relative protein concentrations can be made over a 220 fold concentration range, from an average of 5 ngs to 790 ngs (FIG. 2 and Table 3). As in the Lineweaver-Burke plot of enzyme data, protein concentration and stain density reciprocals aproximate a straight line (FIG. 2).

TABLE 3

Linearity of Recipical Plots of Native Protein Concentration and Staining Density.

| Protein | Linear range | Data Points | Correlation Coefficient | Slope |
|---|---|---|---|---|
| Bovine Serum Alb. | 5–1000 (200×) | 17 | .994 | 11.98 |
| Ovalbumin | 2–1000 (500×) | 18 | .979 | 4.67 |
| B-Lactoglobulin | 7–250 (36×) | 12 | .965 | 21.14 |
| a-Chymotrypsin | 2–500 (250) | 16 | .993 | 36.43 |
| Carbonic Anhydrase | 5–1000 (200×) | 17 | .973 | 57.74 |
| Hemoglobin | 7–1000 (143×) | 17 | .987 | 130.18 |

The P value was <.001 for the correlation coefficients of the data points. Each data point in this table represents the average value obtained from a minimum of 4 experimental determinations.

It is clear from the data presented herein that a rapid, positive silver stain with good contrast has now been developed for membranes and thin layer plates by combining photo-reduction and chemical-reduction methods. Prior art silver stain produces a negative image of proteins on nitrocellulose and lacks contrast between the background and the protein band or spots (Merril et al., *Electrophoresis* 5:289–297, 1984). The combination of a chemical-reduction step with the photo-reduction silver stain has resulted in an unexpectedly sensitive, positive image silver stain with low background staining, allowing for the detection and quantitation of proteins and nucleic acids on thin membranes.

The first step in this new stain protocol employs copper acetate, a metal salt that is both a good fixative and a silver stain enhancer. Without being bound to any theory, it is postulated that the mechanism of copper's stain enhancement may be similar to its action in the biuret reaction in which a characteristic color shift, from violet to pink, is achieved by titrating peptides in the presence of copper ions. Copper complexes formed with the N-peptide atoms of the peptide bonds are responsible for this reaction. Furthermore, there are a number of potential metal-peptide complex sites, other than those at the peptide N-atoms, which may interact with copper. As copper has a greater tendency to donate electrons than silver, indicated by its position in the electromotive series of the elements, any elemental copper formed may displace positive silver ions from solution. Following the treatment with copper acetate, a latent image, or silver nucleation centers are formed, catalyzed by the photo-reduction of ionic to metallic silver. This photo-reduction is achieved by sequentially soaking the membrane in a solution containing chloride and citrate ions and then in a solution containing silver nitrate. The membrane is irradiated with light while it is in the silver nitrate solution. The presence of the resulting silver chloride, in the membrane produces a significant increase in light sensitivity over that which can be achieved with silver nitrate alone. Herman Vogel, a 19th century photochemist, postulated that silver nitrate and silver chloride are synergistic in their response to photo-reduction. He reasoned that although silver chloride is more sensitive to the reducing action of light than silver nitrate, it is fixed in position by its insolubility and the potential density of its image would be limited unless the free silver ions supplied by the silver nitrate are present to diffuse into the photo-reduction centers (Reilly., *The Albumin and Salted Paper Book*, p. 4, 1980). This increase in sensitivity was further enhanced by the presence of acetate and citrate ions (Merril et al., supra; Reilly, supra; Mess, *The Theory of the Photographic Process*, 1st edition, p. 305, 1952). White fluorescent light proved to be the most effective for this photo-reduction. Ultra violet light produced a denser image, but it also produced an unacceptable background stain. Continued irradiation with white light would provide sufficient photo-reduction to produce an image of the protein pattern on the membrane, however, photo-reduction alone usually results in a dense background stain (Merrill et al., supra). It was found that greater sensitivity and contrast could be achieved by limiting the light irradiation to a total of four minutes, only enough to initiate the formation of a latent image. Formation of the visible image was achieved by chemical-reduction.

The chemical-reduction of ionic to metallic silver at the latent image nucleation centers, which leads to the formation of the visible image of the proteins or nucleic acids on the membranes, was effected by placing the membrane in a solution containing the reducing reagents hydroquinone and formaldehyde. These reagents were first employed for the reduction of ionic to metallic silver in photography. Hydroquinone introduced in 1880, is known for its ability to produce photographic images of high density with little background fogging. Formaldehyde as a photographic developer is a relatively weak one. Cajal, in 1903, adapted these reagents for use in silver stains to visualize the histology of the nervous system (*Trab. Lab. Invest. Biol. Univ. Madrid* 2:129–222, 1903; *Trab Lab. Invest. Biol. Univ. Madrid* 3:1–7, 1904; *Heimer Contemporary Research Methods in Neuroanatomy* pp. 106–107, 1970). During image formation, ionic silver is reduced to metallic silver, the formaldehyde is converted to formic acid (*Ehrenfried Photogr. Sci. Tech.* 18B:2–6, 1952) and the hydroquinone to quinone.

Once the image is formed, the unreacted silver chloride must be removed from the membrane, or else the background will have a grayish cast. Furthermore, silver chloride will become increasingly dark as the silver ions are photo-reduced, by exposure to light, to metallic silver. Removal of the silver chloride is accomplished by the use of sodium thiosulfate. Discovered by Herachel in 1839, sodium thiosulfate removes the silver chloride by complexing with it to form a series of complex ergentothiosulfate sodium salts, most of which are soluble in water (Newhall, *Latent Image, The Discovery of Photography*, pp. 57–60, 1983). The last step in the stain requires washing the membrane with water to remove the argentothiosulfate sodium salts, unreacted reagents, and silver grains formed in solution that may have precipitated onto the surface of the membrane.

Plots of the optical density of silver stained proteins versus their concentration produced different staining curves for each of the proteins studied (Table 1, and FIG. 1). Protein specific staining curves has also been observed with most of the organic dye stains, including Coomassie Blue (Fazekas de St. Groth, et al., *Biochim. Biophys. Acta.* 71:377–391; Tal et al., *J. Biol. Chem.* 260:9976–9980, 1985) and with most protein assays such as the commonly used Lowry protein assay (*Biol. Chem.* 193:265–275, 1951). Production of these curves is governed by the basic mechanisms underlying the detection and assay methods. The fact that each protein produces a unique density verses concentration curve in these studies, illustrates a dependence on specific reactive groups contained in each protein. Futhermore, the occurrence of protein-specific curves argues against a stain mechanism that depends on some fundamentall subunit common to all proteins, for example the peptide bond, or a unique element in each protein, such as the terminal amino acid. A stain that depended on a subunit, such as the peptide bond, would result in similar staining curves for all proteins, when the density of staining for each of the protein bands or spots was plotted against the mass of each of the proteins in their respective bands or spots. Similarly, a stain that was based on a reaction with a unique element in each protein, for example the terminal amino group, would produce a similar plot for each protein when their densities were plotted against the number of molecules contained in each respective band or spot. It is possible that these protein-specific curves may be utilized to differentiate proteins and to provide insights concerning the reactive groups responsible for the staining reactions. It also requires a careful choice of a "standard protein(s)" if this stain is used quantitatively to estimate protein concentrations. A protein containing an abnormal number of stain reactive groups would produce a curve which would tend to underestimate the concentration of proteins containing normal numbers of reactive groups.

A study of amino acid homopolymers and individual amino acids was undertaken with the current stain to gain information about specific groups that may be involved in the staining reactions. Cysteine and cystine are the only individual amino acids which stained while poly-methionine and the hydrophilic basic amino acid polymers: poly-lysine, poly-arginine, poly-histidine, and poly-ornithine also stain. The observation of staining of the basic amino acids in their homopolymeric form, but not as individual amino acids, may be related to the shift of pKs that is normally associated with the incorporation of amino acids into peptides. The pKs usually shift toward the neutral range, resulting in an increased presence of ionized amino acid side chains closer to the physiological pH. This type of shift in pK would enhance the ability of a reactive group in an amino acid side chain to form a complex with a metal ion. As an example, a shift in the pk of a side chain containing an amino group would reduce the proton competetion that a metal ion must overcome for the amino group's N-atom electron pair. Staining of the basic amino acid and methionine hompolymers, but not their individual amino acids may also indicate the need for cooperative effects of several intramolecular functional groups to form complexes with the silver or copper ions (Freeman, *Inorganic Biochemistry* 1:121-166, 1973).

Heukeshoven and Dernick also observed silver staining of the basic homopolymers of histidine, arginine, and ornithine, although they did not report staining of the basic amino acid homopolymer poly-lysine (*Electrophoresis* 6:103-112, 1985). The role of the basic amino acids in silver staining is further strengthened by the observation by Nielsen and Brown that the basic amino acids: lysine, arginine, and histidine, (in both a free and homopolymeric form) produce colored complexes with silver (*Anal. Biochem.* 144:311-315, 1984).

Previous studies have reported silver staining with other amino acids. Heukeshoven and Dernick reported silver staining of the homopolymers of glycine, serine, proline and aspartic acid while Nielsen and Brown reported the formation of colored silver complexes with: aspartate, and tyrosine. Staining of these homopolymers was not corroborated in the current study, and prior metal binding studies failed to demonstrate interactions with the side-chain hydroxyl groups of serine, threonine or tyrosine (Freeman, *Inorganic Biochemistry* 1:121-166, 1973). These discrepencies concerning the non-basic amino acids may be due to differences in the staining procedures employed; the Heukeshoven and Dernick study stained homopolymers on polyacrylamide gel, and the Nielsen and Brown study involved the formation of silver-amino acid complexes in solution. The current study utilized membranes and thin layer plates. Also, the previous studies used formaldehyde in an alkaline sodium carbonate solution for image development, while the current study used acidic conditions and a combination of light, hydroquinone and formaldehyde for the image formation. Differences in the underlying mechanisms of alternate silver staining protocols is further indicated by the observation that ovalbumin had a steeper staining slope than albumin in previous silver stain studies (Merril et al., *Electrophoresis* 3:17-23, 1982; Poehling et al., *Electrophoresis* 2:141-147, 1981; Yuksel et al., *Electrophoresis* 6:361-366, 1985), while this relation is reversed with the current protocol.

The importance of both the basic and the sulfur containing amino acids in the current staining protocol was corroborated by observations with purified peptides and proteins of known amino acid sequence. Leucine enkephalin, which has neither sulfur containing nor basic amino acids, did not stain with silver while neurotensin which also has no sulfur containing amino acids but does have three basic amino acid residues (one lysine and two arginines) does stain with this silver stain. Gastrin produced a weak staining reaction. It lacks basic amino acids but it has one sulfur containing amino acid, methionine. Oxytocin stains fairly vigorously. It also has no basic amino acids but is does have two sulfur contaiing cysteines. The staining reaction of angiotensin II was rather anomalous. It produced a negative stain rather than a positive silver stain despite its two basic amino acids, arginine and histidine. All the other polypeptides studied, insulin somatostatin, alpha-melanocyte stimulating hormone, thyrocalcitonin, aprotinin, vasoactive intestinal peptide and ACTH, contained both basic and sulfur containing amino acids and they all produced positive silver staining reactions.

The importance of the basic amino acids was further corroborated by evaluating the relationship between a denatured protein's amino acid mole percentages and its ability to stain with silver. The best correlations were achieved when a comparison was made between the slope of the linear portion of a denatured protein's staining curve and the protein's mole percentages of the basic amino acids, histidine and lysine. A similar correlation was observed by Dion and Pomenti *Anal. Biochem.* 129, 490-496, 1983. Dion and Pomenti suggested a mechanism for the role of lysine in silver staining in which lysine binds with glutaraldehyde. The bound glutaraldehyde then supplies aldehyde groups to reduce ionic silver to metallic silver. While this mechanism may play a role in the stain protocol employed by Dion and Pomenti, it is unlikely to be a factor in the current study, since the protocol of the present invention does not use glutaraldehyde. Prior studies also suggested that alkaline conditions may be important for the formation of silver complexes with lysine and histidine. However, the current protocol utilizes acidic conditions (the silver nitrate and formaldehyde/hydroquinone solutions are acidic, pH 2.03, and pH 4.16, respectively). No significant correlations were found between a protein's amino acid mole percentages and its ability to stain with silver for native, undenatured, proteins. This lack of significant correlation is probably due to the inaccessibility of many of the potentially active amino acid side chains in the undenatured protein structures.

The significant correlation of silver staining intensity to the mole present of lysine ($r=0.94, 0.01>p>0.001$) is most likely due to the reactive "amino group" at the terminus of its side chain. The amino group is one of the most active groups in metal binding due to its strong electron-donor qualities and the ligand-field effect of its nitrogen atoms (Freeman, Inorganic Biochemistry, 1:121-166, 1973). In general, the lower the pk of a potential metal binding group, the more likely it is to form a metal-ligand bond. Given this general rule, one might predict the order of metal binding to be: carboxyl->imidazole>amino groups. However, acid dissociation criterion do not include the role of enthalpy and entropy changes which provide a measure of the relative thermodynamic stabilities of the complex. Reactive group properties, such as the group's electron donor ability and its ligand field effects, must dominate over the acid dissociation constants for the functional groups in the current protocol. This interpretation is supported by the lack of significant correlations between the stain's intensity and the mole percent of the carboxylated side chain amino acids, aspartic or glutamic acid ($r=0.26, P>0.1$ and $r=0.63, P>0.1$, respectively). Furthermore, these carboxylated side chain amino acids did not stain with silver, either as individual amino acids or as homopolymers in our protocol.

Despite the apparent activity of lysine's side chain amino group, neither the amino groups involved in peptide bonding nor the N-terminal amino groups are in themselves sufficient for visualization with the current silver stain. If they were, all of the peptides, proteins, and amino acids would have stained positively. However, the amino groups involved in peptide bonding and N-terminal atoms may be of some importance for the intensity of the stain, as these atoms have been observed to form 13 different complexes with copper between pH 1.5 to pH 11.0 (Osterberg et al., J. Biol. Chem. 243:3038-3042, 1968). Bound copper may be reduced under the conditions of this protocol and then be displaced by silver. Alternatively, silver may also interact directly, but weakly, with these groups.

The contribution of histidine to silver staining, as demonstrated in the homopolymer studies and its correlation in the protein staining studies ($r=0.96, 0.01>p0.001$) is not surprising, since the imidazole groups in the histidine side-chains are often important for metal-binding in metalloproteins such as hemoglobin or myoglobin. The effectiveness of histidine in metal binding is probably due to the fact that imidazole groups are good electron donors (Freeman, Inorganic Biochemistry 1:121-166, 1973). The enthalpy changes in the formation of metal-nitrogen (imidazole) bonds are only slightly less than those found with metal-nitrogen (amino) bonds (Meyer et al., J. Am. Chem. Soc. 92:4210-4215, 19700. This slightly lowered ability of the imidazole group, relative to the amino group, to donate electrons for the formation of metal complexes may be balanced by imidazole's lower pK. The lower imidazole group's pk, in contrast to the higher pK of an amino group, reduces the metal ion's competition with protons for the imidazole's nitrogen atom's electron-pair (Freeman, supra).

The guanidine group in arginine's side chain proved to be less active than either the amino or the imidazole groups in the side chains of lysine and histidine respectively. Arginine's correlation coefficient was not found to be significant in these studies, ($r=0.40, PO.1$). This lack of activity of the quanidine group may have been, in part, responsible for the negative staining reaction of the peptide angiotensin II which contains the two basic amino acids arginine and histidine (one residue of each). However, neurotensin, which contains two arginine residues and one lysine residue, stained fairly well (FIG. 3). Cooperative metal binding effects between the active groups may also play a role in the staining process. In angiotensin II the arginine residue is separated from the histidine by three residues, while in neurotensin the two arginines are adjacent to each other and only one residue separates them from lysine.

Recent studies concerning the mechanisms of Coomassie dye staining of proteins have indicated a similar importance for the basic amino acids. Righetti and Chillemi noted that polypeptides rich in lysine and arginine were aggregated by Coomassie G dye molecules, suggesting that the dye interacts with the basic groups in the polypeptides (Righetti et al., J. Chromatogr. 157:243-251, 1978). Studies of proteins with known sequences, by Tal et al., confirmed these observations and expanded upon them with the demonstration of a significant correlation between the intensity of Coomassie blue staining and the number of lysine, histidine and arginine residues in the protein (J. Biol. Chem. 260L9976-9980, 1985).

Of the nonpolar and uncharged polar amino acids, only the sulfur containing amino acids, methionine, cysteine and cystine, showed any silver staining reactivity in the present studies. Cysteine and cystine were the only amino acids to stain as individual amino acids and they may account for the silver staining properties of the peptide oxytocin. Oxytocin contains no basic amino acids and its only suflur containing amino acids are two cysteine residues. The ability of cysteinyl side-chains to form complexes with silver ions is well known. At the low pHs utilized in this protocol, the predominant species is $Ag(HCys)_2^+$. It has been suggested that the ability of reducing agents [including: thiosulfates, sulfides, borohydrides, cyanoborohydrides, mercaptoethanol, thioglycolic acid, cysteine, tributylphosphine reducing metal salts (such as $FeCl_2$; $SnCl_2$ and $TiCl_3$) and dithiothritol] to intensify silver stains may be related to the generation of thiol groups in cysteine residues (Morrissey, Anal Biochem. 117:307-310, 1981). However, proteins that contain no cysteine or proteins with an alkylated cysteine(s) were also affected by these reducing agents in some stain protocols (Heukeshoven et al., Electrophoresis 6:103-112, 1985).

Methionine's ability to participate in the silver staining process was demonstrated by the staining of the methionine hompolymer. Methionine may also be responsible for the staining of the peptide gastrin. Gastrin contains no basic amino acids and only one methionine residue. In general the thioether sulfur atoms in the methionine residues are weaker electron donors than the sulfhydryl sulfur atoms in the cysteine residues. The only metal ions that have been observed to bind to the thioether's sulfur atoms are those with electons in the $d^8$ and $d^{10}$ configurations ($Pd++$, $Pt++$, $Ag+$, $Cu+$, and $Hg++$). The affinity of sulfur ligands for metal ions may be explained by the highly polarized state of sulfur atoms during interactions with small metal ions containing high charge densities. Sulfur's electron distributions and energies enhance the enthalpies of metal ion bonding (they have high crystal field stabilization energies). There may also be electron resonance bonding in the metal-sulfur bond (Freeman, supra). The negative and relatively insignificant staining correlations achieved with the sulfur containing amino acids methionine and cysteine (r=−0.69,P>0.1 and r=−0.29,P>>0.1 relatively) may indicate their minor role in proteins containing relatively large numbers of basic amino acids. This poor staining correlation is somewhat of a paradox since poly-methionine stained with a higher silver density than the basic amino acid homopolymers. This paradox may be explained by a disruption of cooperative effects between sulfur atoms by the active groups in the basic amino acids in the silver staining process.

In studies of silver staining reactions with nucleic acids and their precursors, the nucleic acid polymers stained fairly well. However, only the purine bases, adenine and guanine demonstrated a positive staining reaction. Neither the nucleosides nor the nucleotides of adenine or guanine stained. Adenine and guanine have free amino groups in the C-6 and C-2 positions, respectively. Given the active metal binding role of amino groups in the proteins, one might have expected these amino groups to be important in the silver staining reaction of these bases. However, if those amino groups were major factors in the staining reaction, then the nucleosides and nucleotide derivatives of these bases should have stained. Schneider et al., Helv. Chim. Acta. 47:992-998 (1964) have suggested that the amino group in a purine base is incapable of forming complexes with metal ions because the potential free electron pair of the amino group is needed to stabilize the electron deficient purine ring. Given the theoretical argument against a simple involvement of the amino group and the observation that the nucleotides and nucleosides do not stain, an explanation of the staining reaction of the free purine bases may involve the nitrogen atom N-9 in the purine ring. The guanine and adenine N-9 position had previously been implicated as the favored binding site for copper ions (Eichhorn, Inorganic Biochemistry, 1:1191-1209, 1973). However, when a purine is incorporated in a nucleoside, nucleotide or nucleic acid, the N-9 nitrogen atom is bound to a ribose or deoxyribose sugar and incapable of binding a metal ion. if this interpretation is correct, the precursor nucleosides or nucleotides may be too weak as individual units to form a complex with a metal ion. However, when these subunits are closely linked in a nucleic acid polymer, cooperative effects of two or more active groups may permit the formation of a complex with a metal ion(s). The amino groups of the purine subunits may be involved in this type of cooperative metal binding. Gilen et al., J. Am. Chem. Soc. 86:2792-2794 (1964) have shown that methylation of adenine's amino grop decreases its affinity for silver. They suggested that adenine's affinity for silver involves a cooperative effect in which a two silver ion bridge is formed between the amino group of one adenine residue and the N-1 atom of another adenine residue. Additional sites on the bases which have been shown to complex with metal ions include the N-3 site of the pyrimidines, and the N-3 site of the purines. Of the three potential metal binding sites in nucleic acids, the base, the ribose and the phosphate, the ribose is, in general, the weakest electron donor while the phosphate is the strongest. However, a study of stability constants of silver complexes formed with: adenosine, AMP, ADP, ATP and DNA, denigrated the role of the phosphate group in silver binding (Weser et al., Z. Naturforsch. 25:592-597, 1970). A number of investigators have speculated that metal ions may form large chelate rings by simultaneously binding to an oxygen in the phosphate group and a nitrogen in the purine or pyrimidine base structure (Eichhorn, Inorganic Biochemistry, 1:1191-1209, 1973).

Consideration of various theories discussed above, of course without being bound thereto, as to the silver staining properties of individual amino acids, their homopolymers, peptides and proteins of known sequence, and the nucleic acids and their precursors, have permitted some insights as to the probable sites of silver interaction. These insights have been enriched by the extensive literature concerning the formation of metal complexes with these biochemical entities. The theories suggest that silver staining of biochemical entities is initiated by the formation of a metal ion complex with a biochemical group, followed by the reduction of the complexed ionic silver to metallic silver. The electron donating properties of the biochemical groups is not sufficient for the reduction of the silver ions because all of the silver stain procedures require either additional photo- or chemical-reduction agents to produce a metallic silver iage. The electron donation centers that initiate the silver ion complex probably act as catalytic sites in which the electon-rich environment of the biochemical metal complexing group aids photo- or chemical-reducing agents in the selective reduction of the silver ions. If the initial biochemical complexing site were involved in the reduction of the silver ion, then additional reducing agents would not be needed. Furthermore, the fact that a gel can be stained, destained, and then restained, also argues for a catalytic role and against an oxidation of the biochemical silver complexing group (Merril et al., Two-dimensional Gel Electrophoresis of Proteins, pp. 93–109, 1984).

The unique silver stain composition and protocol described herein offer unexpected advantages not heretofore possible. It provides a highly sensitive, qualitative method for the detection of proteins and nucleic acids on membranes and thin layer plates detecting nanogram quantitites. Its reproducible staining curves also permit quantitative determination (including the use of the protocol) as a rapid protein or nucleic acid assay. The "linear" portion of the relationship between the stain density and the protein concentration extended over a 33 fold range for native proteins and a 186 fold range for denatured proteins, these values compare well with the "linear" ranges achieved with previous silver stains (Switzer et al., Anal. Biochem. 98:231-237, 1979). A double reciprocal plot permits a quantitative estimation of protein concentration over a wider range than the 33 fold range achieved by analysis of the "linear" portion of the curve of the native proteins. The double reciprocal plot allows the estimation of native protein concentrations over an average range of 220 fold (Table 3 and FIG. 2). Numerous other graphical and nongraphical methods of estimating protein concentrations from nonlinear calibration curves (Coakley et al., Anal. Biochem. 85:90-97, 1978; Stauffer, Anal. Biochem. 69:646-648, 1975) may be utilized as an alternative to the double reciprocal plot method illustrated herein as a method of extending the concentration range of protein estimation.

Of course, when this protocol is used as a protein assay, the correlation between the density of silver staining and the number of basic amino acids in the protein requires the same steps in chosing a protein standard as that noted for the Coomassie method of protein determination (Van Kley et al., Anal. Biochem. 81:485-487; 1977; Tal et al., J. Biol. Chem. 260:9976-9980, 1985). Tal et al., supra noted that the basic amino acid content of proteins ranges between 10-17 mole percent, with a modal content of 13 mole percent, in most proteins. They suggested the use of egg white lysozyme, with a basic amino acid mole percent of 13.2%, which is closer to the modal, as a protein standard for the Coomassie method of protein estimation, rather than the commonly utilized bovine serum albumin, which has a basic amino acid content of 16.5 mole percent. For similar reasons, egg white lysozyme may also prove to be an optimal standard for the silver stain method of protein estimation.

It is understood that the examples and embodiments described herein are for illustrative purposes only and that various modifications or changes in light thereof will be suggested to persons skilled in the art and are to be included within the spirit and purview of this application and the scope of the appended claims.

I claim:

1. A staining system consisting essentially of separate aqueous solutions in distilled or deionized water of:
   (a) cupric acetate up to saturating concentration;
   (b) about 10-50% v/v acetic acid comprising about 0.01 to 0.1M NaCl and about 0.01 to 0.2M citric acid;
   (c) about 10-50% v/v acetic acid comprising about 0.01-0.5M $AgNO_3$;
   (d) about 0.01-0.3M hydroquinone comprising about 0.1% to 10% v/v of a concentrated formaldehyde stock solution; and
   (e) about 0.01 to 0.5M $Na_2S_2O_3$; whereby a positive image stain of electrophoretically separated proteins or nucleic acids fixed on an electrophoretic separation medium is formed when such proteins or nucleic acids are treated with the staining system in a predetermined manner.

2. A method of staining separated proteins or nucleic acids fixed on a separation medium to produce a positive image thereof, comprising the steps of:
   (a) placing a separation medium containing fixed protein or nucleic acid samples in a solution of about 0.1 to 0.4M cupric acetate for about one minute;
   (b) then transferring the separation medium from step (a) to a solution of about 10% v/v acetic acid containing about 0.03M NaCl and about 0.1M citric acid for about one minute;
   (c) then transferring the separation medium to a solution of about 10% v/v acetic acid containing about 0.1M $AgNO_3$ and irradiating the separation medium for about one minute with uniform light;
   (d) then removing the separation medium from the silver nitrate solution of step (c) and again placing the separation medium in the solution of step (b) for about one minute;
   (e) then transferring the separation medium back to the silver nitrate solution of step (c) and irradiating the separation medium for about three minutes with uniform light;
   (f) then tranferring the separation medium of step (e) into a solution of about 0.2M hydroquinone containing about 4% v/v of a concentrated formaldehyde stock solution, for about one minute, or until the proteins or nucleic acids in the separation medium develop an even dark brown color;
   (g) then rinsing the separation medium for about one minute with water, and thereafter immersing the separation medium for about five minutes in a basic solution containing about 0.06M $Na_2S_2O_3$ while gently agitating the separation medium every 30 seconds;
   (h) then washing the separation medium with a stream of tap water flowing parallel to a surface thereof to wash off unbound silver.

3. The method according to claim 2 further comprising determining the amount of the stained proteins or nucleic acids in the separation medium by measuring the image density thereof.

4. The method of claim 2 wherein said separation medium is a membrane or thin layer plate.

5. The method of claim 4 wherein said separation medium is a membrane selected from the group consisting of cellulose acetate, cellulose nitrate, nylon and fibreglass.

* * * * *